United States Patent [19]

Middelburg

[11] Plant 4,287

[45] Aug. 1, 1978

[54] CHRYSANTHEMUM

[75] Inventor: Nicolaas Middelburg, 's Gravenzande, Netherlands

[73] Assignee: Chrysanthemum Breeders Association N.V., Willemstad, Netherlands Antilles

[21] Appl. No.: 828,259

[22] Filed: Aug. 26, 1977

[51] Int. Cl.[2] ..... A01H 5/00

[52] U.S. Cl. ..... Plt./74

[58] Field of Search ..... Plt./74

*Primary Examiner*—Robert E. Bagwill
*Assistant Examiner*—James R. Feyrer
*Attorney, Agent, or Firm*—Boone, Schatzel, Hamrick & Knudsen

[57] ABSTRACT

A new variety of chrysanthemum plant originating as a sport of Horim (unpatented) and characterized by satiny golden blooms, vigorous growth, three month response and permanence.

1 Drawing Figure

BACKGROUND OF THE NEW PLANT

The present invention comprises a new and distinct cultivar of chrysanthemum plant which is a sport of the unpatented off-white chrysanthemum known as Horim. The new cultivar was discovered by Nicolaas Middelburg on Jan. 2, 1975, at 's Gravenzande in the Netherlands, and has been asexually reproduced by cuttings at the same location. The new cultivar has been found to retain its distinctive characteristics through successive propagations.

DESCRIPTION OF THE DRAWING

The accompanying drawing shows the unique characteristics of the new cultivar, the color being as nearly true as possible with color illustrations of this type. The photo shows the new cultivar in various stages of bloom.

DESCRIPTION OF THE NEW PLANT

The new cultivar is a short day response plant and, when grown in the vicinity of 's Gravenzande, Holland, has a response time of about 3 months. The new cultivar may be grown year round under greenhouse conditions.

In the description which follows, color references are made to the "Horticultural Colour Chart II" issued by the British Colour Council in collaboration with the Royal Horticultural Society. The following data is based on observations made at 's Gravenzande, Holland.

Botanical classification: *Chrysanthemum morifolium.*

Bud:
- *Size.*—Medium.
- *Form.*—Short with flat top.
- *Sepals.*—Smooth edge.
- *Calyx.*—Small, smooth, apple shaped.

Color:
- *When sepals first divide.*—Uranium Green 63/3.
- *When petals begin to unfurl.*—Barium Yellow 503/1.
- *Inside of petals when half blown.*—Barium Yellow 503/1.
- *Reverse of petals when half blown.*—Barium Yellow 503/1.

Bloom:

- *Size.*—Medium.
- *Fully expanded.*—6-7 centimeters.
- *Borne.*—Several together.
- *Stems.*—Medium, strong.
- *Form.*—Single (daisy).
- *Permanence.*—Excellent, 4 weeks.

Color:
- *Center of flower.*—Cyprus Green 59/1.
- *Base of petals.*—Agatha Green 60.
- *Inside of petals.*—Barium Yellow 503/2.
- *Reverse of petals.*—Barium Yellow 503/2.
- *Tonality from a distance.*—Barium Yellow 503/2.
- *Discoloration.*—After 3 weeks to Barium Yellow 503/2.

Petals:
- *Texture.*—Thick.
- *Appearance.*—Satiny.
- *Arrangement.*—Imbricated.
- *Persistence.*—Drop off cleanly.
- *Fragrance.*—Slight, typical chrysanthemum.
- *Number.*—Normally 33-36.

Reproductive organs:
- *Stamen, anthers.*—Few, small.
- *Pollen.*—Cadmium Orange 8/1.
- *Arrangement.*—Tucked inside calyx.
- *Styles.*—Columnar.
- *Length.*—Short, thin.
- *Stigmas.*—Dresden Yellow 64.
- *Ovaries.*—Enclosed in calyx.

Plant:
- *Growth.*—Vigorous.
- *Height.*—Medium, depending on culture.

Foliage:
- *Top side.*—Spinach green 0960.
- *Size.*—Medium.
- *Quantity.*—Normal.
- *Ribs and veins.*—Ordinary.
- *Edge.*—Serrated.
- *Underside.*—Smooth, spinach green 0960/2.

I claim:

1. A new and distinct cultivar of chrysanthemum, substantially as described and pictured herein, characterized by its satiny golden blooms, vigorous growth, three month response and permanence.

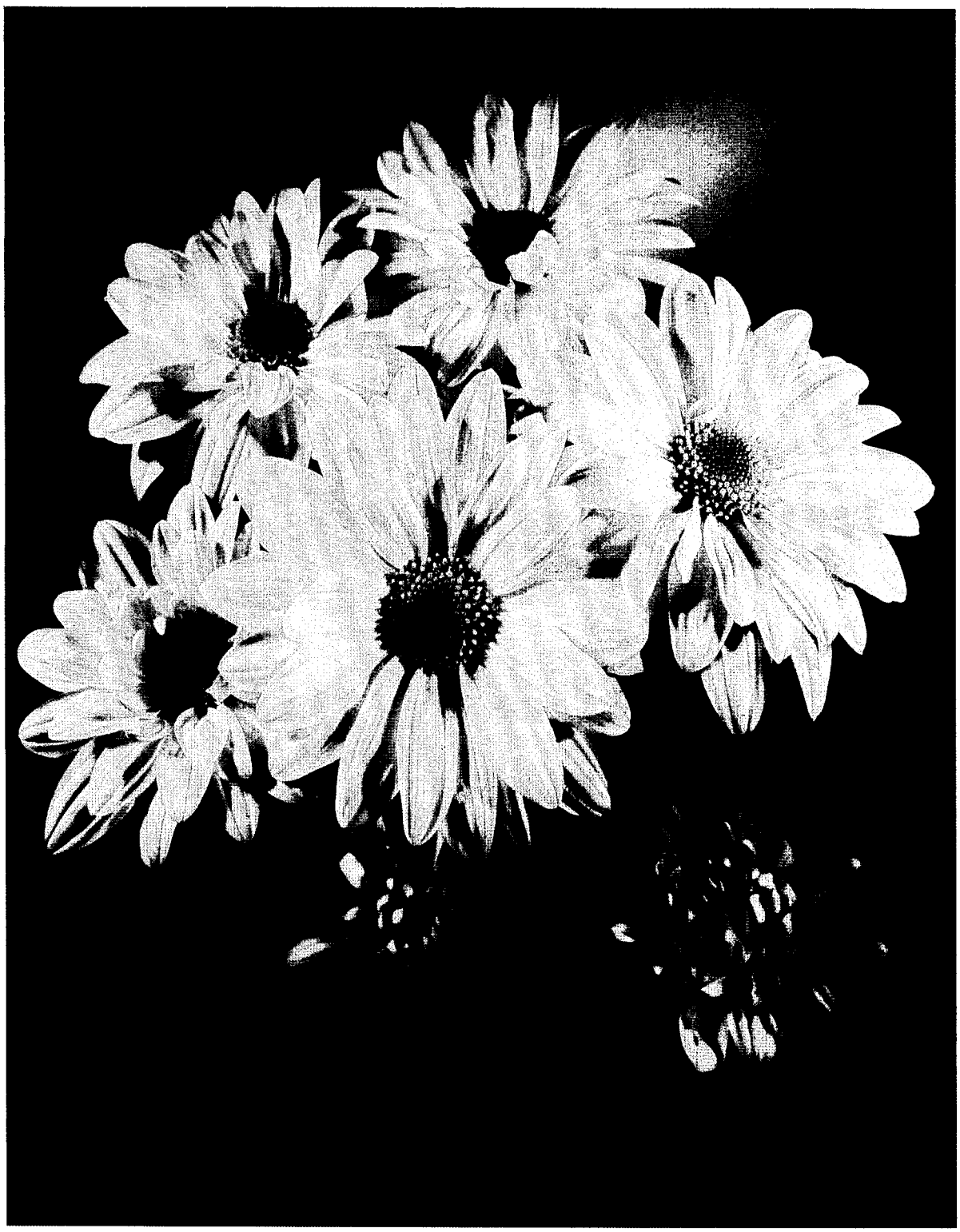

* * * * *